United States Patent [19]

Pagliari et al.

[11] Patent Number: 4,847,232
[45] Date of Patent: Jul. 11, 1989

[54] LIQUID PEROXIDIC COMPOSITIONS

[75] Inventors: Alberto Pagliari, Saronno; Carlo Scotti, Voghera; Roberto Del Bianco; Giorgio Angeloni, both of Milan; Michele Merenda, Frugarolo, all of Italy

[73] Assignee: Ausimont S.p.A., Milan, Italy

[21] Appl. No.: 113,658

[22] Filed: Oct. 28, 1987

[30] Foreign Application Priority Data

Oct. 29, 1986 [IT] Italy ............................. 22167 A/86

[51] Int. Cl.$^4$ ............................................. B01J 31/02
[52] U.S. Cl. ................................ 502/160; 252/186.23; 568/561; 525/387
[58] Field of Search ................. 502/160; 252/186.23; 568/561

[56] References Cited

U.S. PATENT DOCUMENTS

| | | | |
|---|---|---|---|
| 3,118,866 | 1/1964 | Gregorian | 568/561 X |
| 3,787,504 | 1/1974 | Peri et al. | 568/561 |
| 4,202,790 | 5/1980 | Steller | 502/160 X |
| 4,239,644 | 12/1980 | Nambu et al. | 502/160 X |
| 4,450,302 | 5/1984 | Willis | 502/150 |

Primary Examiner—Patrick P. Garvin
Attorney, Agent, or Firm—Stevens, Davis, Miller & Mosher

[57] ABSTRACT

The invention relates to liquid peroxidic compositions containing:

from 1 to 50 parts by weight of a diperoxide of formula:

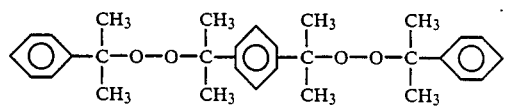

from 5 to 75 parts by weight of dicumyl peroxide;
from 1 to 85 parts by weight of a peroxide of formula:

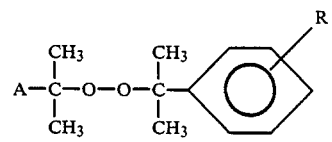

wherein R is H or an alkyl group containing from 1 to 3 C atoms and wherein A is selected from the radical $CH_3$ and the phenyl radical, optionally substituted.

11 Claims, 1 Drawing Sheet

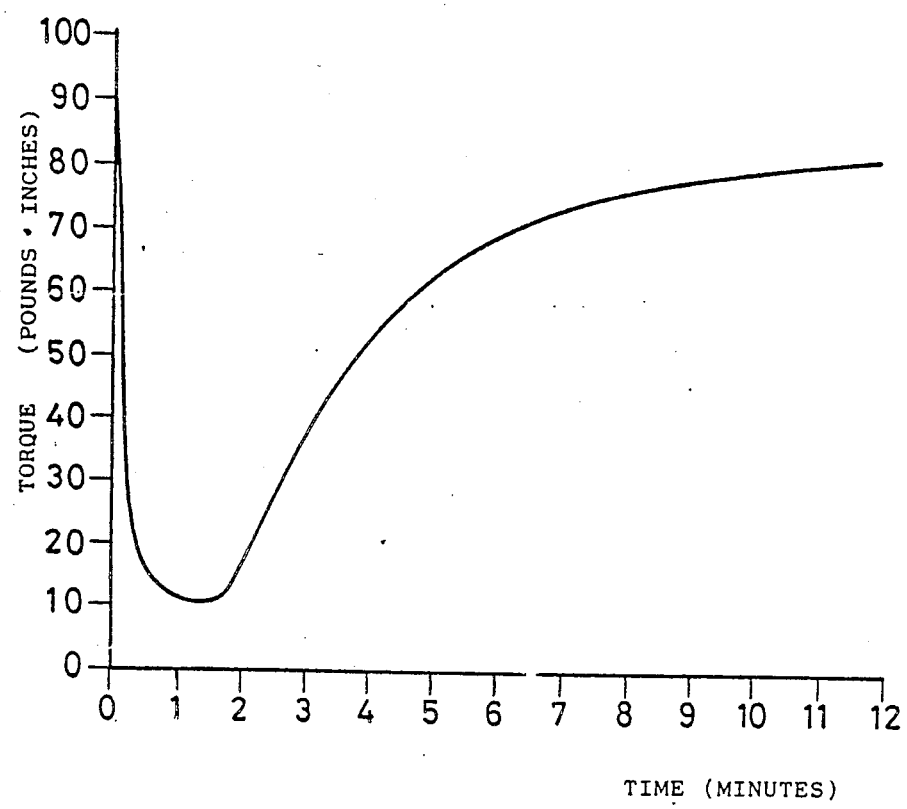

LIQUID PEROXIDIC COMPOSITIONS

BACKGROUND OF THE INVENTION

Italian Pat. No. 1,114,215 describes liquid peroxidic compositions, particularly useful for the cross-linking of polymers (for instance polyethylene or ethylene-propylene elastomers) containing dicumyl peroxide (indicated hereinbelow, for sake of brevity, DCP), a peroxide the use of which (alone) is limited in that, being DCP a solid at room temperature, it is necessary that DCP itself, with the purpose of a more uniform metering (in a continuous operation) be kept in the molten state; such operation often involves a loss of the peroxidic activity and the introduction of impurities. Therefore, the above mentioned Italian Patent suggests the use of balanced peroxy-mixtures, containing an amount of DCP from 5 to 75% together with peroxides which give rise to the formation of liquid mixtures and are comprised in the following general formula (I)

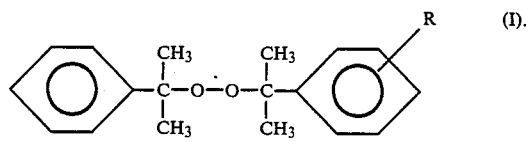

wherein R, in meta or para position, is an alkyl group containing from 1 to 3 C atoms. In particular, peroxides where R represents a methyl group are recommended, whereas according to U.S. Pat. No. 4,202,790, it is more advantageous the use of a peroxide where R is an isopropyl group, namely the use of isopropylcumyl-cumyl peroxide, provided the percentage of DCP in the peroxidic mixture be equal to or higher than 25% and preferably 40% by weight. Said U.S. patent advises to prepare the mentioned peroxides separately (and at temperatures above the room temperature) and thereafter to mix the thus obtained peroxides with DCP, according to the desired ratios.

The Applicant has now found that some particular peroxidic mixtures, different from the mixtures described by said U.S. Patent, give rise to better results, in comparison with the preceding mixtures, and can be prepared and treated in a much simpler and more practical way.

DISCLOSURE OF THE INVENTION

In its widest form the invention is concerning a liquid peroxidic compositions, containing: from 1 to 50 parts by weight of a diperoxide of formula (II):

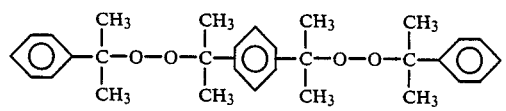

the two substituting groups of the central aromatic ring being in meta and/or para position and the meta/para isomeric ratio being from 1.2 to 2.5 and better from 1.5 to 2.1; this peroxide is commercially known as "PEROXIMON 169";

from 5 to 75 parts by weight of dicumyl-peroxide (DCP);

from 1 to 85 parts by weight of a peroxide having formula (III):

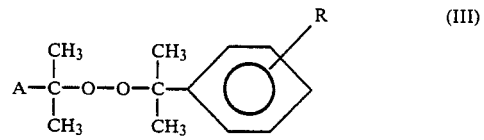

where R is H or a 1-3 Calkyl group, and A is selected from the radical $CH_3$, the phenyl radical and the substituted phenyl radicals. When R is H, A should represent preferably the radical $CH_3$ and when R is the isopropyl radical, A should be preferably selected from the radical $CH_3$ and the phenyl radical; the group R can be in meta and/or para position, the meta:para isometric ratio being preferably in the range from 1.2 to 2.5 and better from 1.5 to 2.1.

Said peroxide of formula (II) was already described in U.S. Pat. Nos. 3,787,504 and 3,118,866, the content of which is an integrating part of the present application. The new compositions differ from DCP in that they are liquid at room temperature and therefore can be incorporated into a polymer without any previous melting; furthermore, they can be easily proportioned and the mixing operation can be performed in a very safe manner. Very uniformly finished articles can be thus very easily obtained.

Unlike the previously known products of formula (I), the diperoxide of formula (II) owns a cross-linking power (on polyethylene) higher than that of DCP and therefore it is not necessary to increase the amount, as in the case of mixtures containing DCP and peroxides of type (I); the increase of the amount, as to liquid mixtures, containing DCP and peroxides of type (I) is generally between 20 and 35% by weight.

The compositions according to the invention are liquid and therefore it is possible to avoid more easily the presence of impurities; in fact, it is easier, in our case, to detect and remove extraneous substances if incorporated.

The cross-linking efficiency of the new compositions may be compared with that which can be obtained using pure DCP and as the mixing of liquid compositions with a polymer (in an extruder) does occur very easily, the working of the polymer is simplified. The polymers which can be cross-linked by the new compositions are generally olefin and vinyl thermoplastic polymers, as well as elastomeric polymers. More particularly, it is possible to mention: middle, low and high density polyethylene, poly-butene-1, ethylene/vinylacetate copolymers, acrylic ester-ethylene copolymers, ethylene/propylene copolymers, ethylene/butene-1 copolymers, ethylene/4-methylpentene-1 copolymers and propylene/butene-1 copolymers; furthermore, we add elastomeric polymers or copolymers such as for instance ethylene/propylene copolymers of the type EP or EPDM, butyl rubber, chlorinated polyethylene and the propylene/butene-1 copolymer.

Also mixtures of at least two olefinic thermoplastic polymers, mixtures of at least two polymers of elastomeric type and mixtures of at least one olefinic thermoplastic polymer with at least an elastomeric polymer can be successfully cross-linked. The new compositions can be used not only for the cross-linking of compact articles, obtained by extrusion or molding, but also for producing expanded cross-linked articles derived from the same materials, in particular from polystyrene containing self-extinguishing agents (antiflame agents);

moreover, the same compositions can be used to promote the decomposition of polymers which are decomposed by peroxides (for instance polypropylene or poly-4-methyl-pentene-1) and as a radical polymerization initiator.

The processes which may lead to the compositions according to the invention are different. According to a preferred embodiment, benzene is alkylated with an excess of propylene, in the presence of $AlCl_3$ and according to generally used techniques such as Friedel-Crafts reaction, thus obtaining a di-isopropylbenzenic mixture (prevailingly meta and para); this mixture is oxidized, always by generally used techniques, until a prefixed amount of dihydroperoxide, corresponding to the desired titre of diperoxide of formula (II) is obtained, besides the mono-hydroxide. The resulting oxidized mixture, containing unreacted hydrocarbons, as well as the corresponding monohydroperoxides and dihydroperoxides, is then reduced, for instance by sulfides, sulfites or sulfohydroxides (according to generally used techniques), so that all the hydroperoxy groups are changed to alcoholic groups (hydroxy groups) and the obtained reduced mixture is uncompletely distilled; a rectified mixture is thus obtained, containing a mono-alcohol having formula (VI):

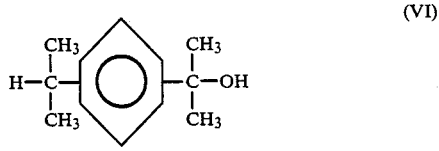

(VI)

and up to 30% by weight of a di-alcohol having formula (IV):

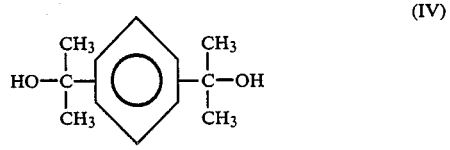

(IV)

together with lower amounts (up to 15%) of unconverted hydrocarbons. Depending on the composition of the desired peroxidic mixture, there are then added, in some cases, amounts of particular alcohols (equal to or different from the preceding ones), in particular cumyl alcohol of formula (V) (see forward).

The mixture containing the alcohols, anyhow prepared is then allowed to react with a cumene mixture (deriving, for instance, from the intermediate step of an usual plant for the synthesis of phenol), containing higher amounts of cumene hydroperoxide and up to 10% by weight (on the hydroperoxide) of cumyl alcohol having formula (V):

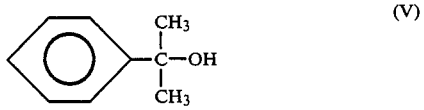

(V)

(common component of generally handled cumenic mixtures) in the presence of one of the commonly used acid catalysts described in U.S. Pat. Nos. 4,266,081; 4,239,644; 4,202,790; and 2,668,180, which supply also the operative conditions; paratoluensulfonic acid, especially when gradually added in one single dose or in portions, has proved particularly effective also at relatively low temperatures (lower than 40° C.).

Before using the resulting peroxidic mixture, it must be carefully washed, for instance with an alkali metal solution; it is important that the reaction synthesis be performed under an inert atmosphere, for instance under nitrogen. The washed peroxidic mixture must be concentrated, thus removing any compound having low boiling temperature (essentially diisopropylbenzene and cumene), preferably by steam distillation. In some cases, it is possible to add a peroxide of formula (III) directly to the peroxidic mixture obtained following the above mentioned operations. The following examples illustrate the invention, without limiting it in any way.

EXAMPLE 1

A rather great amount of benzene was alkylated with two mols of propylene, in the presence of $AlCl_3$ and according to usual Friedel-Crafts techniques, thus obtaining a mixture of diisopropylbenzenes; this mixture was then oxidized, always by generally used techniques, thus obtaining an oxidized mixture (containing para-diisopropylbenzene, meta-diisopropylbenzene, para-di-isopropylbenzene mono-hydroperoxide, para-di-isopropylbenzene dihydroperoxide, metal-diisopropylbenzene monohydroperoxide and meta-di-isopropylbenzene dihydroperoxide). Said oxidized mixture was then reduced with sodium hydrosulfide (NaHS), according to usual techniques, so that all the hydroperoxy groups (—O—O—H) were converted into alcoholic groups (hydroxy groups). Thereafter the resulting reduced mixture was distilled off; a rectified mixture was thus obtained containing 84.8% by weight of a mixture of isopropyl-cumyl monoalcohols (35% of para+65% of meta) and 4.7% by weight of isopropyl-cumyl dialcohols (35% para+65% meta).

133 g of said rectified mixture were loaded into a glass round-bottomed flask provided with stirrer, thermometer and vacuum tap; thereafter, 171.7 g of a cumene mixture containing 78.5% by weight of cumene hydroperoxide, 7% by weight of cumyl alcohol (V) and 10% by weight of nonoxidized cumene were added; there were present:

(a) 0.632 mol of mono-alcohol + 0.032 mols of di-alcohol;

(b) 0.886 mol of cumene hydroperoxide + 0.088 mol of cumyl alcohol.

Thereafter, 71 g of an aqueous solution containing 70% by weight of para-toluensulfonic acid were added, gradually, within 30 minutes, at 25°–28° C. under nitrogen and the mixture was allowed to react, at 25°–28° C., for 3.5 hrs, under stirring. After the end of the reaction, the acidic aqueous phase was separated in a separatory funnel and 2 washings were carried out, using each time 200 cm³ (at 60° C.) of an aqueous 10% by weight NaOH solution, followed by other two washings, using each time (at 60° C.), 200 cm³ of deionized water. After having removed the cumene, by steam distillation, and after having dehydrated under vacuum at 65° C., the resulting peroxidic mixture contained an oxygen amount corresponding to 4.7% by weight and showed a purity degree equal to 91% by weight (total peroxydic content), a density of 0.098 g/cm³ and a viscosity (at 25° C.) equal to 126 mPa.s. Half life values of the mixture (thermal decomposition) were 113° C. (after 10 hours) and 188° C. (after 1 minute); the analysis showed that the mixture contained:

| | |
|---|---|
| di (cumylperoxy)-diisopropylbenzene (meta/para) (PEROXIMON 169) | 4% by weight |
| dicumyl-peroxide (DCP) | 13% by weight |
| isopropylcumyl-cumyl peroxide (meta/para) | 73% by weight |

The remaining 10% was consisting of hydrocarbons and/or unreacted alcohols. Isopropylcumyl-cumylperoxide is known on the marked as PEROXIMON 168.

EXAMPLE 1/a 100 parts by weight of an ethylene-propylene elastomeric copolymer, known by the trade name DUTRAL COO 54, were mixed with 0.3 parts by weight of sulfur, 5 parts by weight of ZnO and 50 parts by weight of carbon black. To the mix there were added 3.46 parts by weight of the peroxidic mixture of example 1 and the resulting blend was homogenized in a calender; the product obtained from the calender had the following properties:
(a) data of the ODR curve at 170° C. (oscillation arc=3°; oscillation frequency=100 cycles/minute; see FIG. 1);
MH=82.6 inch pounds
$t_{s10}$=102 seconds
$t_{90}$=456 seconds A ODR curve (Oscillating Disc Rheometer) has a course (flow) of the type indicated in FIG. 1 and is plotted by the aid of a rotating disc rheometer, according to ASTMD-2084-71T standards.

On the abscissa there are reported times and on the ordinate the twisting torque (inch pounds, measured by means of a dynamometer) opposed by the polymer to the rotation of the disc; in our case the highest cross-link density is revealed by the highest value of the torque (MH=82.6 inch pounds) which does no more vary with the time. Expressions $t_{90}$ and $t_{s10}$ respectively represent the time necessary to reach a twisting moment equal to 90% of the highest twisting moment and the time necessary to reach a level of 10 inch pounds above the lowest point of the ODR curve.

As to other details we refer to U.S. Pat. No. 4,015,058
(b) "scorching" times at the Mooney viscosimeter (at 135° C.):
$ts_{10}$=738 seconds
$ts_{15}$=900 seconds As "scorching" we mean the untimely vulcanization which takes place (undesirably) during the extrusion of the blend, before its outlet from the die; this premature vulcanization its often causing a shut down of the operations.

As scorching time $ts_{10}$ or $ts_{15}$ (at the Mooney viscosimeter) we mean the time necessary to reach an increasing of the lowest value of the viscosity equal to 10 to 15 Mooney units respectively. The viscosity must be determined by means of a cutting disc Mooney viscosimeter (see ASTM D 1646-81 Standards).

EXAMPLE 2

18.8 g of the rectified alcohol of Example 1 were loaded into the same glass round-bottom flask, provided with stirrer, together with 74 g of a mixture containing 85% of cumyl alcohol and 10% of cumene (obtained by reducing 78% commercial cumene hydroperoxide); thereafter 36 g of dialcohol of the diisopropylbenzene (solid; 65% meta+35% para) and finally 205 g of 78.5% by weight of commercial cumene, containing 7% by weight of cumyl alcohol and 10% by weight of cumene were added. On the whole were present:
0.09 mol of m/p-diisopropylbenzene monoalcohol;
0.19 mol of the m/p-diisopropylbenzene dialcohol;
0.568 mol of cumyl alcohol;
0.233 mol of cumene;
1.059 mol of cumene hydroperoxide Thereafter 71 g of a 70% b.w. aqueous solution of para-toluensulfonic acid were added within 30 minutes; then the mixture was allowed to react for 3 hours, the temperature being adjusted between 25° C. and 28° C. By further working as in Example 1, 210 g of a liquid product were obtained, having the following composition:
alpha, alpha'-bis (cumylperoxy)diisopropylbenzene (PEROXIMON 169)=33% by weight
dicumylperoxide (DCP)=57% by weight
isopropylcumyl-cumylperoxide (PEROXIMON 168)=103% by weight This product had an active $O_2$ content equal to 6.1% a freezing point lower than $-5°$ C. and a viscosity at 20° C.=50 mPas; half life values of the mixture (thermal decomposition) were 116° C. (at 10 hours) and 179° C. (at 1 minute).

EXAMPLE 2/a 100 parts by weight of a polyethylene blend, suitable for cable insulation, manufactured by B. P. Chemicals Co. and known by the trade name HF NM 4993, were admixed with 2.5 parts by weight of the peroxidic mixture of Example 2 and the resulting mixture was homogenized in a calender; the product coming out from the calender was molded by compression and tested at the ODR rheometer at 180° C. (oscillation arc=5°) thus obtaining the following results:
MH=78 inch pounds;
$t_{s2}$=66 seconds; $t_{90}$=288 seconds.

Analogously to what described in example 1, $t_{s2}$ indicates the time necessary to reach a level of 2 inch pounds above the lowest point of the ODR curve.

EXAMPLE 3

250 g of a mixture containing 57% by weight of cumene hydroperoxide, 30% by weight of cumyl alcohol and 10% by weight of cumene, obtained by partial reduction of commercial cumene hydroperoxide (78.5% by weight) were loaded into a round-bottom flask provided with stirrer; thereafter 37 g of a meta/-para mixture (65% meta+35% para) of diisopropylbenzene dialcohol were introduced. On the whole 0.94 mol of cumene hydroperoxide, 0.55 mol of cumyl alcohol and 0.19 mol of meta/para diisopropylbenzene dialcohol were present. Then, 71 g of a 70% by weight aqueous solution of para-toluensulfonic acid were introduced within 30 minutes and under stirring, while keeping the reaction temperature between 25° and 30° C.; the mixture was allowed to react at this temperature for 3 hours. By working as in Examples 1 and 2, 190 g of a product (liquid at room temperature), containing 60% by weight of dicumyl peroxide and 35% of di(cumylperoxy)diisopropylbenzene were obtained; 21 g of tert-.butylperoxide were added. At the end a product was obtained, containing 32% by weight of di(cumylperoxy)diisopropylbenzene (PEROXIMON 169), 54% by weight of dicumylperoxide (DCP) and 10% by weight of tert.butyl-cumylperoxide; this final liquid composition showed the following characteristics:

freezing point: lower than −5° C.;
viscosity at 20° C.: 45 mPas;
active oxygen content: 6.2% by weight.

Half life times were 117° C. (at 10 hours) and 181° C. (at 1 minute). Tert.-butyl-cumylperoxide is commercially known as "PEROXIMON 166".

EXAMPLE 3/a 100 parts by weight of the polyethylene blend of Example 2/a were admixed with 2.5 parts by weight of the peroxidic mixture of example 3 and the resulting blend was homogenized in a calender; by working as in Example 2/a the following results were obtained:
MH=85 inch-pounds
$t_{s2}$=54 seconds; $t_{90}$=300 seconds.

Analogously to what described in U.S. Pat. No. 4,015,058, the content of which is integrating part of the present application, the quality of a peroxidic composition can be easily evaluated by calculating an efficiency factor (E) according to the equation:

$$E=(MH.t_{s2}):(t_{90}-t_{s2})$$

The following table reports the efficiency factors obtained in the examples:

| | COMPOSITION OF THE PEROXIDIC MIXTURE | | | | |
|---|---|---|---|---|---|
| Ex | PEROX-IMON 169 | DCP | PEROX-IMON 168 | PEROX-IMON 166 | E = MH. $t_{s2}$ $t_{90}-t_{s2}$ |
| 2/a | 33% | 57% | 10% | — | 23,19 |
| 3/a | 33% | 57% | — | 10% | 18,65 |
| 4 | 2% | 57% | 41% | — | 13,25 |

In Examples 2/a and 3/a the presence of PEROXIMON 169, on which the invention is based, gives an efficiency much higher in comparison with Example 4 where the diperoxide is almost completely replaced by a monoperoxide (PEROXIMON 168).

EXAMPLE 4

Example 3/a was repeated by replacing almost all the diperoxide or formula (III), according to the invention, by a comparable amount of PEROXIMON 168, thus obtaining the following results:
MH=50 inch pounds;
$t_{s2}$=66 seconds; $t_{90}$=315 seconds.

What we claim is:

1. Liquid peroxidic compositions containing:
from 1 to 50 parts by weight of a diperoxide of the formula (II):

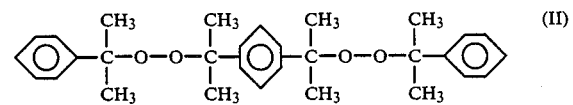

the two substituting groups of the central aromatic ring being in meta and/or para position and the meta/para isomeric ratio being between 1.2 and 2.5;
from 5 to 75 parts by weight of dicumyl-peroxide;
from 1 to 85 parts by weight of a peroxide of the formula

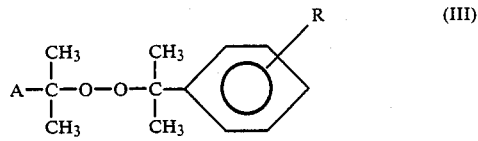

wherein R is H or an alkyl group containing from 1 to 3 C atoms, and wherein A is selected from the radical CH₃ and the phenyl radical.

2. Compositions according to claim 1, containing from 50 to 70 parts by weight of dicumyl-peroxide.

3. Compositions according to claim 1 or 2, wherein the meta/para isomeric ratio, for the peroxide of formula (III) is from 1.2 to 2.5.

4. Compositions according to claim 1, wherein the meta/para isomeric ratio, for the diperoxide of the formula (II), is from 1.2 to 2.5.

5. Compositions according to claim 1, containing:
from 20 to 45 parts by weight of diperoxide of formula (II), wherein the meta/para isomeric ratio is from 1.2 to 2.5;
from 50 to 70 parts by weight of dicumyl-peroxide;
from 1 to 25 parts by weight of a peroxide of the formula:

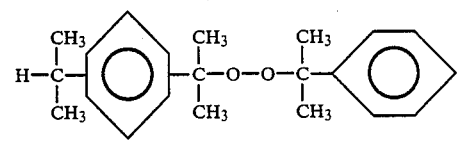

6. Compositions according to claim 1, containing:
from 20 to 45 parts by weight of diperoxide of formula (II),
from 50 to 70 parts by weight of dicumylperoxide;
from 1 to 25 parts by weight of a peroxide of the formula;

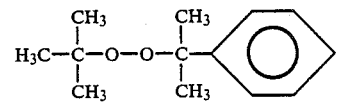

7. A process for the manufacture of a composition according to claim 1, comprising:
(a) the oxidation of meta- and/or para-diisopropyl-benzene, by which oxidation an oxidized mixture is formed, containing a major amount of isopropylcumyl mono-hydroperoxide and up to 12% by weight (on the mono-derivative) of the corresponding di-hydroperoxide;
(b) the reduction of said oxidized mixture, by which reduction a reduced mixture is formed, wherein the hydroxyl groups (alcoholic groups) replace the hydroperoxidic groups of said oxidized mixture;
(c) an optional distillation of said reduced mixture, to obtain a concentrated mixture, containing a major amount of isopropylcumyl mono-alcohol and up to 30% by weight of the corresponding di-alcohol (optionally dissolved in the starting hydrocarbon);
(d) an optional admixture with additional amounts of cumyl alcohol and/or m/p-diisopropylbenzene dialcohol, so that the amounts of dicumyl-peroxide and- /or of the diperoxide of formula (II) in the final liquid peroxidic compositions are increased; and (e) the reaction with a cumenic mixture, containing a major amount of cumene hydroperoxide and up to 10% by weight (on the hydroperoxide) of cumyl alcohol.

8. A process according to claim 7, wherein the reaction under (e) is performed in the presence of para-toluensulfonic acid, at a temperature equal to or lower than 40° C.

9. A liquid peroxidic composition according to claim 1, wherein the meta/para isomeric ratio is between 1.5 and 2.5.

10. A liquid peroxidic composition according to claim 3, wherein the meta/para isomeric ratio for the peroxide of formula (III) is from 1.5 to 2.1.

11. A liquid peroxidic composition according to claim 4, wherein the meta/para isomeric ratio for the diperoxide of formula (II) is from 1.5 to 2.1.

* * * * *